United States Patent

Pensel et al.

[11] Patent Number: 5,867,308
[45] Date of Patent: Feb. 2, 1999

[54] MICROSCOPE, IN PARTICULAR FOR SURGICAL OPERATIONS

[75] Inventors: Jürgen Pensel, Eichberg, Switzerland; Herbert M. Stüttler, Rankweil, Austria

[73] Assignee: Leica Mikroskopie Systeme AG, Switzerland

[21] Appl. No.: 817,634

[22] PCT Filed: Oct. 25, 1995

[86] PCT No.: PCT/EP95/04178

§ 371 Date: Jun. 30, 1997

§ 102(e) Date: Jun. 30, 1997

[87] PCT Pub. No.: WO96/13743

PCT Pub. Date: May 9, 1996

[30] Foreign Application Priority Data

Oct. 26, 1994 [CH] Switzerland ............................ 3217/94

[51] Int. Cl.[6] ............................. G02B 21/00; G02B 21/22
[52] U.S. Cl. ............................ 359/368; 359/379; 359/376
[58] Field of Search .................................. 359/368, 379, 359/380, 376; 250/201.3; 351/210

[56] References Cited

U.S. PATENT DOCUMENTS

| | | | |
|---|---|---|---|
| 3,723,932 | 3/1973 | Cornsweet et al. ...................... | 351/210 |
| 4,973,149 | 11/1990 | Hutchinson ............................... | 351/210 |
| 5,231,674 | 7/1993 | Cleveland et al. ....................... | 351/210 |

FOREIGN PATENT DOCUMENTS

| | | | |
|---|---|---|---|
| 2 272 124 | 5/1994 | United Kingdom ............. | G02B 7/28 |
| WO 93/14454 | 7/1993 | WIPO ............................... | G06F 3/00 |

OTHER PUBLICATIONS

Informatique 92; Proceedings: "International Conference Interface To Real and Virtual Worlds", 27 Mar. 1992, Nanterre, FR, p. 659; J. Charlier et al., Command Par Le Regard D'Un Systeme De Visualisation 2D: Exemple Du Microscope Operatoire (with translation).

Funkschau, vol. 5, 1990 DE, pp. 66–67, K. Fellbaum et al., "Sprache–electronisch im Griff", see p. 67, col. 1–3, paragraph 1; figures 7, 8 (with translation).

"Patent Abstracts of Japan", vol. 17, No. 464 (P–1599), 24 Aug. 1993 & JP, A, 05 108252 (NEC Corp), Apr. 30, 1993.

*Primary Examiner*—Jon Henry

[57] ABSTRACT

A microscope (23A) has a sensor or eye pupil tracking device (3A) and preferably a device for representing symbols of control elements by means of which various functions or accessories of the microscope may be actuated by eye movements.

27 Claims, 4 Drawing Sheets

MICROSCOPE, IN PARTICULAR FOR SURGICAL OPERATIONS

BACKGROUND OF THE INVENTION

The invention involves a microscope, in particular an operation microscope.

The prior art knows two main groups of microscopes:
(1) one-tube monocular microscopes and
(2) two-tube stereomicroscopes.

Adjusting elements for the optical components of the microscope and/or for work tables are known for both variants.

Since the user as a rule concentrates on observing the object viewed through the microscope, such adjusting elements must be situated in the area between the objective and the eyepiece, so that the user can reach them well.

In various applications, in particular, however, in operation microscopes, it is difficult for a user (operating surgeon) to operate the microscope in this way, since, as a rule, he needs both hands to carry out the operation or the manipulation of the object. To make things easier for the users in such situations, electrically driven adjusting elements were developed that undertook the desired settings or adjustments via a remote control (electric switch). In order to free the user's hands completely, foot switches with which various limited adjustments, such as zoom, focus, etc., could be undertaken were attached to the microscope.

In operations in particular, however, it is not easy for a user who is concentrating on a field of view and his hands to coordinate additional movements of his feet to operate various foot switches or the like. Therefore in the course of extensive further developments voice-operated adjustment elements were created that were operated by the user by means of speech. Speech-recognition software is not yet free of errors, however, and especially in the stress of an operation there is the danger that an operating error of the microscope could occur through a misinterpretation of a command, which could have catastrophic consequences for the patient in certain difficult operations. In addition, the speech-recognition software as a rule is not suitable for understanding different users or must store the speech profiles of all users through extensive voice rehearsals, which means considerable costs and reduces the availability of the microscope. Mouth switches were also developed that in the first place were uncomfortable and in the second place could hardly be used with the necessary oral protection.

Obviously various eye-tracking methods are known. Since the beginning of 1994 at least the camera for autofocussing of the Canon company that was mentioned has been known. A French report "Informatique 92" developed a complete system as of 1992 in which a microscope is controlled by means of eye-tracking in such a way that when an operating surgeon changes his direction of sight through the tube (e. g. he looks to the left), the microscope changes its position in space and orients or swings the tubes to the new direction of sight of the operating surgeon. This procedure is not used in practice, since it is often not at all desired by the operating surgeon possibly to lose what had previously been seen from the angular field. In addition, the automatic adjustment of the microscope in accordance with this known teaching leads to the fact that the microscope, which was originally focussed correctly, can suddenly become unfocussed in the center of its direction of sight, since as a rule the Z distance also changes through the swivelling of the tubes. Only at low magnifications or in microscopes with built-in external autofocussing (not eye-oriented) could this system possibly find practical application.

A Japanese publication JP-A-51108252 refers to an eye-controlled cursor in a computer as of 1993. As a user looks at a computer monitor, he is watched, so that his eye movements can control what happens on the screen. This prior art, however, lies outside microscopy, and it also does not provide any indication of the teaching in accordance with the invention. The control of microscope drives or something like that is not suggested. The same is true for U.S. Pat. No. 4,973,149, which previously proposed watching the user's eyes while looking at a computer monitor and so giving the user the possibility of controlling the computer or his environment. WO-A-93/14454, which also dates from 1993, refers to the control of a computer monitor by means of eye-tracking.

SUMMARY OF THE INVENTION

On the basis of the prior art that has been mentioned and the disadvantages associated with it, the invention thus has the basic objective of overcoming the problems that have been mentioned and creating a corresponding remotely-controlled microscope for users whose hands should not be encumbered with operating the microscope and in particular suitable operating controls for the microscope. The new microscope should ensure complete freedom of movement for the hands and avoid excessive burdening of the user's feet. Further, the new microscope should be quite suitable for integration in computer-supported systems with various cooperating modules, such as in videostereomicroscopy, videostereotaxy, etc. and other applications in which at least one remotely-controlled or automatic function (e. g. autofocussing or autozoom) is provided. The new operating controls should be small in size and be easy to integrate in the microscope.

This objective is attained in an exemplary manner for the first time through the application of the characteristics of claim 1, in connection with which a sensor is understood to mean any device that can detect an eye movement or a nerve command for an eye movement and derive from it the eye movement that is carried out or planned.

What is preferred is to build an eye or pupil position detection device into at least one tube of the microscope. In accordance with the invention, this detection device is linked with an electronic analysis unit that detects the pupil position on the basis of a certain pupil position of a user who is looking through the microscope and from this deduces certain adjustment commands of the user and passes these on to the electromechanical adjustment elements.

Within the scope of the invention there are also variants having one pupil detection device per tube. In order to avoid misunderstandings in detection for users with visual defects, however, it is preferred to use only one detection device. Preferably this could be one of the two provided—depending on the user3 s choice. A setting on the leading eye of the user in question is recommended.

It is thus possible for the user to issue a command very quickly (eye movements are among the fastest movement capabilities of a human being) and unambiguously through gazing at markings in the tube, for example, or at images, symbols, or the like reflected in the tube.

When a microscope in accordance with the invention is integrated in a computer-supported system that encompasses, for example, other remotely-controlled devices, image generation devices, operating instruments, etc., markings could be provided, if needed, for all the functions of these devices, so that the user can issue control commands in a similar manner as on a screen-active (user-active) computer monitor surface. Instead of a mouse he simply uses his glance to designate the corresponding symbols. The activation of the appropriate symbol or command here can take place through the user's gazing for a long time at the symbol in question or looking back and forth between two symbols within a specific time period. To show the user that his command has been recorded, the symbol can then change its color, for example, it can begin to blink, or be replaced by another symbol; acoustic display possibilities also lie within the range of the invention.

Combinations with already known remote control mechanisms, however, also lie within the scope of the invention, e. g. with a foot switch that in contrast to known examples has only one function, e. g. that of "clicking on" or activating a corresponding symbol. Simplified voice controls that, for example, only require a sound from the user when the latter gazes at a certain symbol also lie within the scope of the invention.

To bring the control symbol to be viewed into the user's field of view various methods are conceivable, including: glass panes or something similar with appropriate markings (such as a reticle with peripheral markings or the like) installed in the light path, e. g. points of light produced by LEDs on the interior of the tube, e. g. LCD screens superimposed via beam splitters, etc. In this regard, it may be advantageous to specify calibration procedures in which at the beginning of use the observer looks at a certain place, e. g. a reticle in the tube and thereafter initiates a calibration routine through a switch or automatically in which the control device determines which pupil position corresponds to the gaze at the specific place or the reticle in order to be able to evaluate positions deviating from this better. Alternatively it is also possible to design the specific place, e. g. the reticle, to be movable on a suitable carrier in order to make the direction of sight coincide with the specific place at an arbitrarily selected eye position—e. g. one that is optimal for the user—so as to have an appropriate reference from it when control commands are given through turning the eyes from this position. In this process the command fields that are visible for the eye are tracked on the display surface turned towards the eye, for example. Other procedures may also be used at the beginning of a session to find a reference, to the extent that they are suitable for determining the relative movement of an eye from a certain position.

In order to detect the pupil position there are also different variants within the scope of the invention among which preference is given to one in which a measurement beam from an IR laser is scanned from the eye surface optically by means of a CCD in order to detect the eye or pupil position in this way. In this regard reference is also made to the "eye control" process, which as such is known in another field—video technology—as brought on the market by the Canon company, for example, under the trademark UC-XlHi. The data obtained through the device provided there for detecting the eye position are used there, among other things, to turn an autofocus function of the camera lens to a specific area in the field of vision of the cameraman. Of course the scope of this application also includes variants in which an autofocus system of a microscope operates in conjunction with the optical operating controls or symbols and the control associated with them in such a way that the autofocus follows the gaze of the user to focus the microscope sharply on the particular limited detailed area on which the user is concentrating. As alternatives to the optical detection of eye movements there are also all the other procedures within the scope of the invention in which movements or nerve impulses for movement commands are perceived and analyzed from other body areas. Thus the movements of the eye muscles, for example, can also be sensed via electrodes or the like in order to detect the viewing position of the eye.

A variant in which operating control symbols in the user's field of view permit freely programmable functions provides special advantages. In this regard there is an especially favorable combination with the device known on the market as "Leica Box," which makes all kinds of data from all kind of equipment, measuring devices, and electronic memories, etc. usable for image processing and rapid data evaluation. In this regard reference is made to the Swiss application of the applicant with the file number 01091/94-3 which is a priority application regarding the published international patent application WO95/27917, the teaching of which is considered to have been disclosed as lying within the scope of this application for the purpose of a possible and sensible combination of the two teachings.

For several different users it is advantageous if settings that have been made at one time are stored and retrieved when needed, so that after the selection of a setting stored for a specific user the microscope can be used immediately without further calibration or adjustment efforts.

Further reference is made to the teachings of the Swiss application of the applicant with the file number 01092/94-5, which is a priority application regarding the published interational patent application WO95/27918, since the small superimposition elements disclosed there can find optimal utilization in the microscope in accordance with the invention. In connection with the measurement of the distance between the main objective and object or object detail being viewed that may be necessary, reference is made to the teaching of the Swiss application of the applicant with the file number 01090/94-1, which is a priority application regarding the published international patent application WO95/27917 and is regarded as being disclosed here for the purpose of presenting a further design variant of the invention. This involves in particular the figures and associated descriptive parts. For focus measurement in the area of the object viewed by the eye, for example, image signal processing can also be employed, which measures the edge sharpness of certain contours, for example, deduces from this the imaging sharpness, and actuates the corresponding adjustment elements to improve the imaging sharpness.

To protect the retina from excessive IR radiation when the user eye is illuminated by means of an IR diode, the IR diode in accordance with an elaboration of the invention is pulsed in time with the CCD readout rate, the CCD readout rate being preferably chosen freely.

Further details and characteristics of the invention are revealed and characterized in the patent claims. To this extent the foregoing presentation does not restrict the invention. The disclosure of all variants and design forms arises from the overall text of the application, which includes the claims.

BRIEF DESCRIPTION OF THE DRAWINGS

Using some exemplified embodiments that are presented by means of sketches, the invention is explained in greater detail using examples. The following is shown.

DETAILED DESCRIPTION OF THE PREFERRED EMBODIMENTS

The figures are described coherently. The same reference numbers indicate the same components. Components having similar functions bear the same reference numbers with different subscripts.

Figure 1:
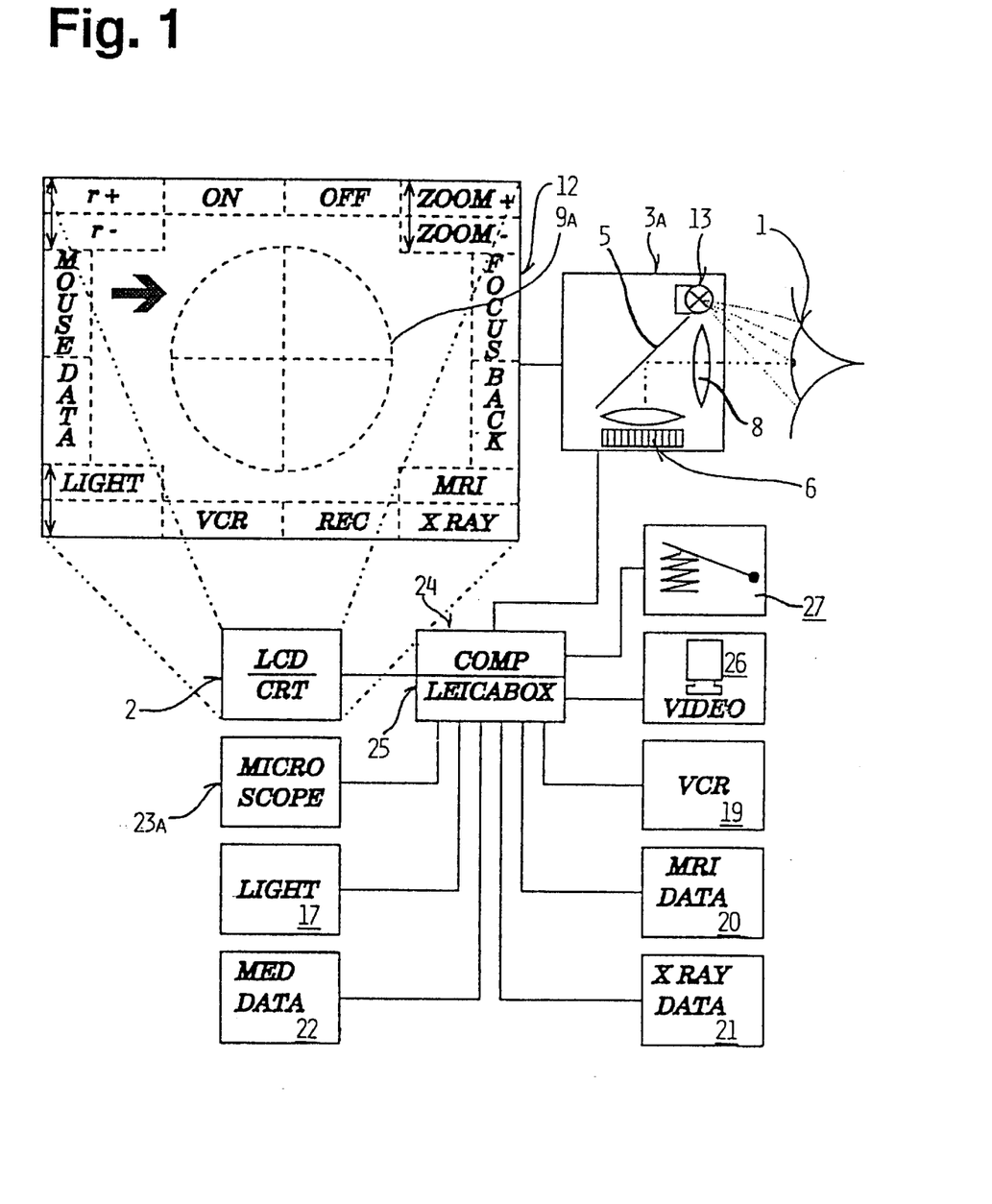
FIG. 1 a block diagram with a selection of possible functions and devices that can be remotely controlled by means of the optical operating controls in accordance with the invention, FIG. 2 a symbolic arrangement in which the symbols from an LCD are superimposed via a beam splitter in the eyepiece light path, FIG. 3 a symbolic design of an operation microscope with facilitated application and capabilities in accordance with the invention, and FIG. 4 a detail of a microscope in which a single picture taking device serves both to detect the pupil position and to take a picture of the object.
Figure 2:
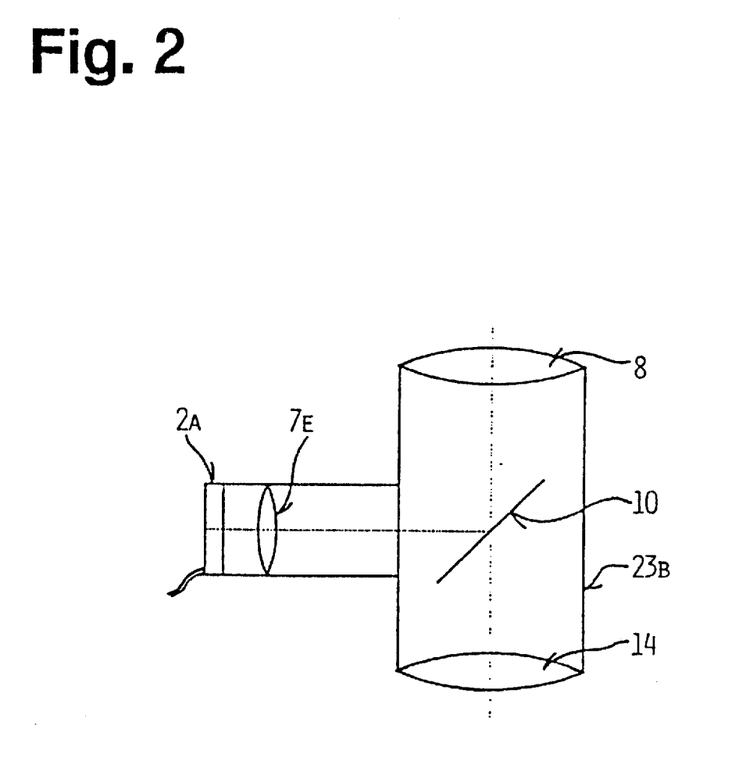

FIG. 1 shows with 12 the image that is presented to a viewer who looks through an eyepiece into a tube of a microscope 23 in accordance with the invention. What is not seen in the picture here is the object, which possibly could also be seen; it is placed optically under the display field of the picture 12. For the examples presented it is not important whether the view of the object is made possible purely through optical components or whether possibly a video signal processing device is also inserted, such as, e. g. a videoendoscope, which also lies within the scope of this invention. FIG. 2 shows how the picture 12 is reflected in the tube light path of the microscope 23b. An LCD or CRT display 2a throws the image generated by a data processor 24 via an optical system 7e and a splitter mirror 10 through an eyepiece lens 8 into an eye of the viewer 1. In FIG. 1 such an LCD or CRT is designated with 2. In the case of a videoendoscope or an operation microscope with an LCD or CRT display as object reproduction unit, the separate optical superimposition of an image can be dispensed with, if the latter is linked electronically with the image of the object.

On the right next to the picture 12 FIG. 1 shows symbolically a pupil position detection device 3a, which is shown in outline and comprises the eyepiece lens 8 and a semireflecting mirror 5 —which preferably acts a mirror only for infrared light—via which a CCD 6 or the like scans the position of the pupil of a viewer eye 1. In this process the pupil is illuminated by an IR LED 13, so that the geometric form of the pupil can be portrayed clearly on the CCD 6. By means of image processing, which is not further indicated, e. g. in the data processing unit 24, the pupil position information that is scanned in this manner is evaluated and through this a determination is made of where the eye in picture 12 is looking. In this way one can determine at which of the fields designated with barred lines in 12 the eye is looking in order to be able to derive from it the appropriate desired commands. In the variants shown a foot switch 27 is also provided by means of which a function previously selected with the eye is actuated, "clicked on."

An incomplete selection of examples of possible commands and functions is enumerated: switching the command field 12 on/off; for the microscope 23a magnification can be chosen (Gamma) and the zoom setting can be changed. Automatic focus tracking can take place in such a way that the pupil position detection device 3 always determines the place on the object at which the eye is looking in order to focus the microscope 23a on this place after that; the control of a video camera 26 that is attached to the microscope; control of a video recorder 19; e. g. also with an instant replay function according to which the last seconds of the procedures are displayed again on the LCD or CRT to give the user orientation assistance; a superimposition of the image of the object with a similarly positioned image of an MRI image 20 or an X-ray image 21 or something similar; control of the illumination 17 of the microscope 23a; superimposition of data referring to patients (med data) 22, such as blood pressure, EKG, pulse, etc.; aside from the functions that have been described a movable "mouse" can also be displayed surface-actively as a cursor, which can be controlled through eye movement, as is possible with a mouse with a computer monitor. Positioning the "mouse" in a part of the picture with subsequent confirmation through the foot switch can correspondingly also initiate the functions that have been described or other supplementary functions such as marking a specific place for immediate or later image data processing, for drawing contour lines, etc.

As a rule, all functions and controls of the devices that have been described are directed by the data processing unit. For faster data processing a data preparation unit 25, which converts all data formats, some of which are different, to a common processible format or converts command data into appropriate apparatus control data, is installed in front of this data processing unit 24.

Figure 3:
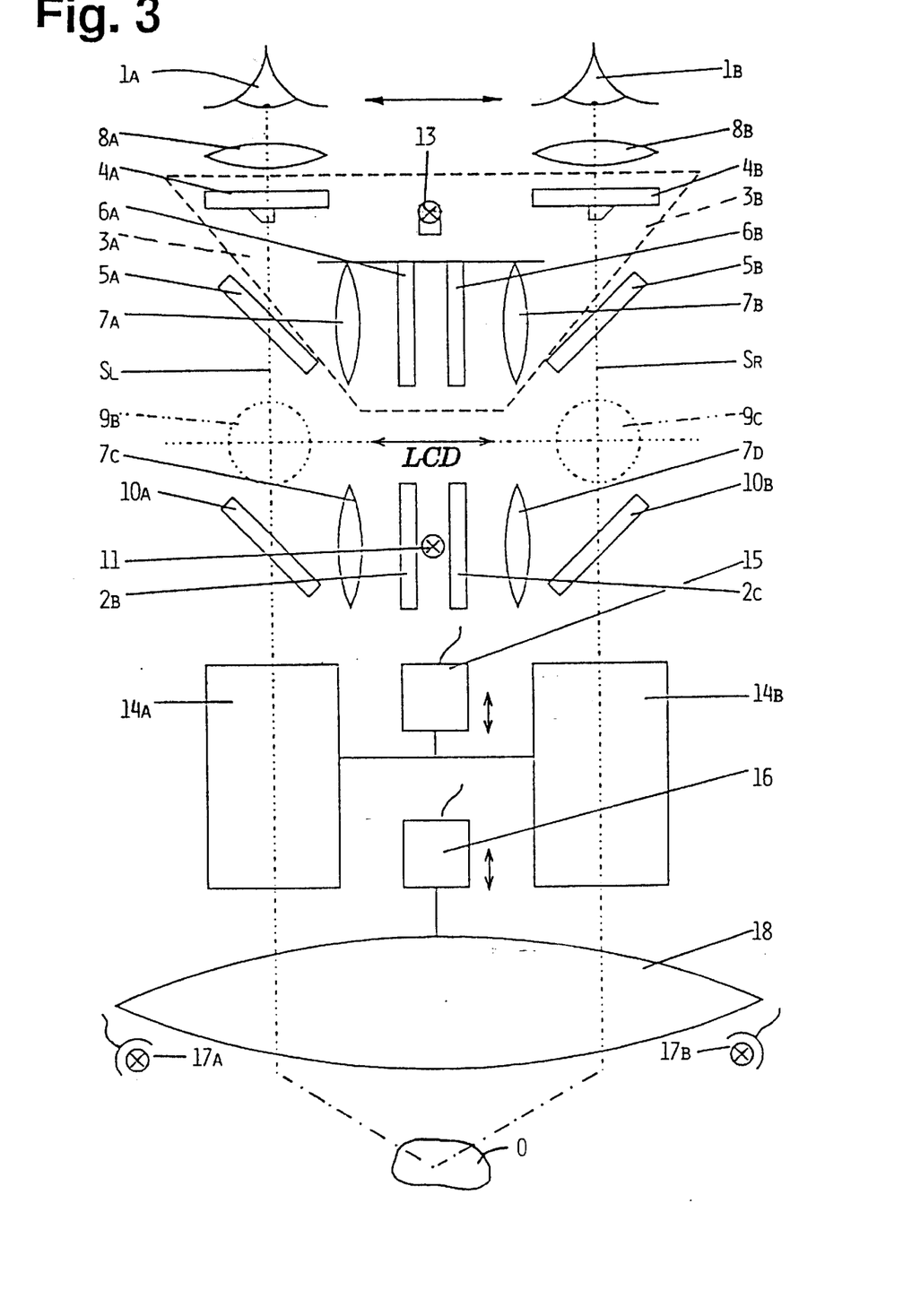

FIG. 3 shows schematically a main objective 18, which itself, as indicated, or the adjustable optic systems of which, which are not shown, can be controlled through a focussing drive 16, and a microscope illumination 17. Further a zoom 14 with corresponding zoom drive 15 is provided.

Splitter mirrors 10 serve to reflect image information from two LCD's 2a,b, each of which is allocated to one of the two light paths. The LCD's reproduce the image 12 and any MRI, X-ray, or patient data. Behind the LCD's a background illumination 11 is located. The optic systems 7c and d provide good imaging. The reticles 9b and c, which, e. g. are inserted on movable glass plates in each light path and are used for calibration purposes, are portrayed symbolically and rotated by 90° in the image plane.

Partially transparent IR mirrors 5a,b permit a free view through to the object in the visible range. IR beams, on the other hand, are imaged via the optic systems 7a and b on the CCDs 6a and b, the optic systems 7a and b being designed in such a way that the pupil of a viewer's eye 1 is imaged on the CCDs. Preferably, however, only one eye is always taken into account alternatively in order to avoid misunderstandings in the evaluation in the event of visual defects or the like.

The eyes are illuminated through the eyepiece lenses 8a and b and/or by an IR LED 13 independently to make possible the imaging on the CCD 6 that was mentioned. In the case of illumination through the eyepiece lenses 8, 8b, small superimposition elements 4a or b are installed in front of them that transmit IR illumination to the viewer eyes via small reflecting surfaces. So long as the light used for illumination is sufficiently scattered, the place where the small reflecting surface is attached is not critical. In the event of concentric low-scatter illumination by means of light cones on the center of the eyeball surface, it would be preferable for the small reflecting surface to be located axially in the light path as far as possible.

The subject of FIG. 3 shows in addition a further aspect of the invention, in particular for stereomicroscopes, which can also be applied independently. Since two pupil position detection devices 3a,3b are provided, each of which portrays the pupil positions independently of one another on the CCD 6a or 6b, this design permits the automatic setting of the eye interval by means of a drive that is not further portrayed, which, depending on the interpupillary distance that is measured from the middle of the light path, moves the two tubes toward each other in such a way that both pupils have optimal vision through the microscope. A microscope outfitted in this manner operates practically automatically, and it is sufficient for a viewer to look though it to achieve the most important required settings. If these settings have already been determined ahead of time and stored, it is enough to indicate the user concerned, e. g. by means of entering a code in an operation field with the keyboard or by means of entry via a selector switch, etc.

Figure 4:
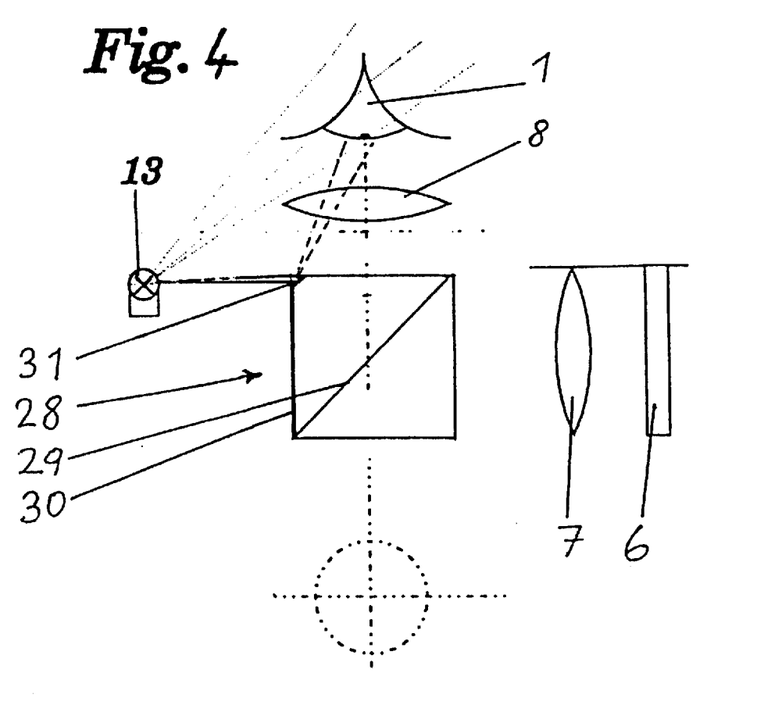

Not further shown because known in the prior art are reflective devices for a video camera or the like. FIG. 4, however, shows a splitter cube 28 that can be employed within the scope of the invention but also independently of it with advantage on the splitter surface 29 of which the image that is seen of the object is thrown laterally through an optical system 7 on a camera CCD 6, while the other part is available for the eye 1. At the same time IR radiation coming from the eye to the splitter surface 29 is reflected laterally to the left to meet there on a mirror surface 30 from which it is also thrown on the CCD 6 through the splitter surface 29 and the optical system 7. It is expedient for the eyepiece lens and the other optic systems in the light path that are not shown to be harmonized in such a way that the object and the eye surface are imaged on the CCD adequately to find out computationally the necessary information about the pupil position from the superimposed image and afterwards to extinguish again the record of the IR radiation. The advantage of such a design lies in dispensing with a second CCD. As a special feature of the splitter cube 28 mention should also be made of the optionally provided bezel 31, which also is designed to be reflecting—especially for IR radiation—and thus guides the beams from the IR diode 13 to the eye 1.

The invention deals further with an aspect that also can be applied independently of what has been said up to this point: In the eyepiece area a positioning support for the head or face of a user is preferably provided, which serves as a horizontal and/or vertical reference and/or relief holding device through stabilizing facial parts of the user. Such a positioning support achieves in the process the objective of ensuring that a setting of the microscope that has once been selected as correct and usable can be assumed again after the user has removed his head from the microscope. This is an advantage above all in operations that last for a long time. In addition there is the effect that fatigue symptoms of an operating surgeon through previous constant neck muscle exertion are reduced.

Of course the pupil position detection device is equipped with a switch that interrupts the measuring routine and consequently also the setting routine as soon as the pupil position detection device no longer can make out any pupils.

Reference Number List

| | |
|---|---|
| 1a,b | Viewer eyes |
| 2a,b,c | LCD or CRT for display in the eyepiece light path |
| 3a,b | Pupil position detection device |
| 4a,b | Superimposition element |
| 5a,b | Semi-reflecting IR mirror (reflection rate for IR radiation about 100%, for other radiation about 0%) |
| 6a,b | CCD or functionally similar sensor for determining the pupil position |
| 7a,b,c,d,e | Imaging optic systems |
| 8a,b | Eyepiece lens |
| 9a,b,c | Reticle |
| 10a,b | Splitter mirror |
| 11 | LCD background illumination |
| 12 | Exemplary image of the LCD or CRT as seen through the eyepiece 8 for eye 1 superimposed on the image of the object viewed |
| 13 | LED for IR light, possibly strobed |
| 14a,b | Zoom |
| 15 | Zoom drive |
| 16 | Focussing drive |
| 17a,b | Illumination |
| 18 | Main objective |
| 19 | Video recorder to play back and record video images |
| 20 | Image generation device for MRI data from the object viewed |
| 21 | Image generation device for X-ray data from the object viewed |
| 22 | Image information generator for patient-related information such as name, age, blood pressure, heart function, etc. |
| 23 | Microscope |
| 24 | Data processing |
| 25 | Data preparation for data format standardization (Leica Box) |
| 26 | Video camera |
| 27 | Foot switch |
| 28 | Splitter cube |
| 29 | Splitter surface |
| 30 | Mirror surface especially for IR beams |
| 31 | Reflecting bezel |
| O | Object |
| SL | Light path (middle) |
| SR | Light path (middle) |

What is claimed is:

1. A microscope for surgical operations comprising:

an eyepiece tube for holding an eyepiece;

means for presenting an image to a user looking through said eyepiece, said image including a microscope operating control symbol;

a microscope adjustment control for controlling an adjustment function of said microscope, said adjustment control corresponding to said operating control symbol;

sensor means for detecting the pupil position of the user's eye and generating a signal representing said pupil position;

data processing means connected to said sensor means for evaluating said signal to determine whether the gaze of said user coincides with said operating control symbol, said data processing means also being connected to said adjustment control for providing a control signal thereto; and actuating means connected to said data processing means for enabling non-manual activation of said adjustment control through said control signal if said gaze coincides with said operating control symbol;

whereby said adjustment control may be operated by the user without use of his or her hands.

2. The microscope according to claim 1, wherein said image includes a plurality of said microscope operating control symbols and said microscope includes a plurality of said microscope adjustment controls each corresponding to a different one of said plurality of operating control symbols.

3. The microscope according to claim 2, wherein said plurality of microscope adjustment controls includes an autozoom function control.

4. The microscope according to claim 2, wherein said plurality of microscope adjustment controls includes an autofocus function control.

5. The microscope according to claim 2, wherein said plurality of microscope adjustment controls includes an illumination function control.

6. The microscope according to claim 2, wherein said plurality of microscope adjustment controls includes at least one adjustment control for controlling the function of a peripheral device operatively connected to said microscope.

7. The microscope according to claim 6, wherein said peripheral device superimposes an MRI image with an object image viewed by said user.

8. The microscope according to claim 6, wherein said peripheral device superimposes an X-ray image with an object image viewed by said user.

9. The microscope according to claim 6, wherein said peripheral device superimposes medical data regarding a patient undergoing surgery with an object image viewed by said user.

10. The microscope according to claim 6, wherein said peripheral device is a video-camera.

11. The microscope according to claim 6, wherein said peripheral device is a video-recorder.

12. The microscope according to claim 1, wherein said sensor means comprises a pupil position detection device having an LED emitting infra-red light toward said eye and a CCD for scanning light reflected by said eye to generate said signal.

13. The microscope according to claim 1, wherein said microscope is a stereomicroscope having a pair of said eyepiece tubes for holding a pair of said eyepieces.

14. The microscope according to claim 13, wherein said sensor means comprises a pair of pupil position detection devices associated one with each eye of said user, each of said pupil position detection devices having an LED emitting infra-red light toward said associated eye and a CCD for scanning light reflected by said associated eye to generate said signal.

15. The microscope according to claim 14, further comprising an interpupillary distance setting device for automatically adjusting the center-to-center spacing between said eyepiece tubes, and wherein said sensor means provides pupil position information to said interpupillary distance setting device to automatically conform the center-to-center spacing between said eyepiece tubes to the interpupillary distance of said user.

16. The microscope according to claim 14, wherein only said signal from a selected one of said pair of pupil position detection devices is evaluated by said data processing means.

17. The microscope according to claim 12, wherein said pupil position detection device comprises a semi-reflecting mirror arranged to redirect said light reflected by said eye to said CCD, said semi-reflecting mirror transmitting light in the visible range but reflecting light in the infra-red range.

18. The microscope according to claim 12, wherein said pupil position detection device includes optical means for directing an object image to said CCD in addition to light reflected by said eye.

19. The microscope according to claim 1, wherein said data processing means includes user programmable memory for storing and automatically retrieving a plurality of user-specific microscope adjustment settings.

20. The microscope according to claim 19, wherein said plurality of adjustment settings includes an interpupillary distance setting.

21. The microscope according to claim 1, wherein said actuating means comprises a foot switch.

22. The microscope according to claim 1, wherein said actuating means comprises an acoustic switch.

23. The microscope according to claim 1, further including a reticle in the microscope's light path for presenting a viewing target to said user for establishing a calibrated reference pupil position.

24. The microscope according to claim 1, wherein said means for presenting an image includes a user-active display surface to which a cursor symbol is allocated, said cursor symbol following pupil movement tracked by said sensor means.

25. The microscope according to claim 6, further including a data preparation unit connected to said data processing means for converting signal data from said peripheral device to a form compatible with said data processing means, and converting said control signal from said data processing means to a form compatible with said peripheral device.

26. The microscope according to claim 1, further including a positioning support near said eyepiece for stabilizing the face of said user.

27. The microscope according to claim 18, wherein said data processing means separates information concerning said object image from information concerning said eye, whereby said information concerning said eye may be selectively extinguished.

* * * * *

UNITED STATES PATENT AND TRADEMARK OFFICE
CERTIFICATE OF CORRRECTION

PATENT NO. : 5,867,308
DATED : February 2, 1999
INVENTOR(S) : Jürgen Pensel, et al.

It is certified that error appears in the above-identified patent and that said Letters Patent is hereby corrected as shown below:

ON THE TITLE PAGE:
Add item --[56] References Cited

U. S. PATENT DOCUMENTS

| EXAMINER INITIAL | | PATENT NUMBER | | | | | | ISSUE DATE | PATENTEE | CLASS | SUBCLASS | FILING DATE IF APPROPRIATE |
|---|---|---|---|---|---|---|---|---|---|---|---|---|
| | | 5 | 0 | 9 | 4 | 5 | 2 | 2 | 03/10/1992 | Sourdille et al. | | | |
| | | | | | | | | | | | | | |

FOREIGN PATENT OR PUBLISHED FOREIGN PATENT APPLICATION

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | DE | 4 | 0 184 | 0 | 0 | A1 | 06/08/1990 | Germany | | | | |
| | | | | | | | | | | | | | |
| | | | | | | | | | | | | | |

Signed and Sealed this

Fifth Day of October, 1999

Attest:

*Attesting Officer*

Q. TODD DICKINSON

*Acting Commissioner of Patents and Trademarks*